(12) United States Patent
Sjolin et al.

(10) Patent No.: US 10,130,313 B2
(45) Date of Patent: Nov. 20, 2018

(54) DATA ACQUISITION FOR COMPUTED TOMOGRAPHY

(71) Applicant: Prismatic Sensors AB, Stockholm (SE)

(72) Inventors: Martin Sjolin, Stockholm (SE); Mats Persson, Vasterhaninge (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 15/594,800

(22) Filed: May 15, 2017

(65) Prior Publication Data

US 2018/0042561 A1 Feb. 15, 2018

Related U.S. Application Data

(60) Provisional application No. 62/373,408, filed on Aug. 11, 2016.

(51) Int. Cl.
| | | |
|---|---|---|
| *A61B 6/03* | (2006.01) | |
| *A61B 6/00* | (2006.01) | |
| *G06T 11/00* | (2006.01) | |
| *G01N 23/046* | (2018.01) | |
| *G01T 1/24* | (2006.01) | |

(52) U.S. Cl.
CPC ............ *A61B 6/032* (2013.01); *A61B 6/4014* (2013.01); *A61B 6/5235* (2013.01); *A61B 6/545* (2013.01); *G01N 23/046* (2013.01); *G01T 1/247* (2013.01); *G06T 11/003* (2013.01); *G06T 2207/10081* (2013.01)

(58) Field of Classification Search
None
See application file for complete search history.

(56) References Cited

U.S. PATENT DOCUMENTS

| | | | | |
|---|---|---|---|---|
| 5,416,817 | A | * | 5/1995 | Ruehrnschopf ....... G01T 1/2985 378/19 |
| 2008/0170658 | A1 | | 7/2008 | Pack et al. |
| 2015/0324973 | A1 | | 11/2015 | Ueki et al. |
| 2017/0090046 | A1 | * | 3/2017 | Danielsson ............. G01T 1/242 |
| 2017/0091962 | A1 | | 3/2017 | Hagiwara |
| 2017/0269008 | A1 | * | 9/2017 | Sjolin .................. G01N 23/046 |

FOREIGN PATENT DOCUMENTS

| | | |
|---|---|---|
| EP | 0467532 A2 | 6/1991 |
| EP | 1501052 A1 | 1/2005 |
| WO | 2017082785 A1 | 5/2017 |

OTHER PUBLICATIONS

Jul. 3, 2017, International Search Report issued for related International Application No. PCT/SE2017/050496.
Martin Sjölin, et al., Optimal sinogram sampling with temporally offset pixels in continuous rotation CT, Medical Imaging 2017: Physics of Medical Imaging, Mar. 2017, pp. 1013221-1-1013221-13, vol. 10132, SPIE.
Martin Sjölin, et al., Angular oversampling with temporally offset layers on multilayer detectors in computed tomography, Medical Physics, Jun. 2016, pp. 2877-2883, vol. 43, No. 6.

* cited by examiner

*Primary Examiner* — Thomas R Artman
(74) *Attorney, Agent, or Firm* — Young & Thompson

(57) ABSTRACT

There is provided a method and corresponding system for data acquisition, for Computed Tomography, CT, based on an x-ray imaging system (10) having a detector (12) with a plurality of pixels (13), wherein data sampling is performed with a temporal offset between measurements acquired by adjacent pixels of the detector.

2 Claims, 13 Drawing Sheets

DATA ACQUISITION FOR COMPUTED TOMOGRAPHY

TECHNICAL FIELD

The proposed technology generally relates to x-ray imaging and more particularly to a method of data acquisition, for Computed Tomography, CT and a corresponding system, computer program and computer program product as well as a corresponding Computed Tomography, CT, system.

BACKGROUND

Radiographic imaging such as x-ray imaging has been used for years in medical applications and for non-destructive testing.

Normally, an x-ray imaging system includes an x-ray source and an x-ray detector system. The x-ray source emits x-rays, which pass through a subject or object to be imaged and are then registered by the x-ray detector system. Since some materials absorb a larger fraction of the x-rays than others, an image is formed of the subject or object.

It may be useful to begin with a brief overview of an illustrative overall x-ray imaging system, with reference to FIG. 10. In this non-limiting example, the x-ray imaging system 10 basically comprises an x-ray source 11, an x-ray detector 12 and an associated image processing device 15. In general, the x-ray detector 12 is configured for registering radiation from the x-ray source 11 that may have been focused by optional x-ray optics and passed an object or subject or part thereof. The x-ray detector 12 is connectable to the image processing device 15 via suitable analog processing and read-out electronics (which may be integrated in the x-ray detector or detector system 12) to enable image processing and/or image reconstruction by the image processing device 15. An example of a commonly used x-ray imaging system is a Computed Tomography (CT) system, which may include an x-ray source that produces a fan or cone beam of x-rays and an opposing x-ray detector or detector system for registering the fraction of x-rays that are transmitted through a patient or object. The x-ray source and detector system are normally mounted in a gantry that rotates around the imaged object.

Development in the CT field makes increasingly high gantry rotation speeds and higher spatial resolution of the detectors possible; with this, the requirement for sufficient angular sampling increases. Insufficient angular sampling in CT leads to aliasing which destroys the reconstructed images by introducing streak-like artifacts from sharp edges. Several approaches for oversampling in CT, such as flying focal-spot (FFS) and quarter detector offset (QDO), have been developed, and are predominantly used standard methods, in order to decrease the risk of aliasing. Both the number of samples and the grid on which the sinogram is sampled determine the risk for aliasing.

SUMMARY

It is desirable to find an improved mechanism for managing aliasing in CT systems.

It is an object to provide a method of data acquisition, for Computed Tomography, CT.

It is also an object to provide a system for data acquisition, for Computed Tomography, CT.

Another object is to provide a Computed Tomography, CT, system.

Yet another object is to provide a computer program for enabling, when executed by a processor, data acquisition, for Computed Tomography, CT.

Still another object is to provide a computer-program product comprising a computer-readable medium having stored thereon such a computer program.

These and other objects are met by embodiments of the present invention.

According to a first aspect of the proposed technology, there is provided a method of data acquisition, for Computed Tomography, CT, based on an x-ray imaging system having a detector with a plurality of pixels, wherein data sampling is performed with a temporal offset between measurements acquired by adjacent pixels of the detector.

In this way, a custom sampling pattern, such as a hexagonal sampling pattern, e.g. one that reduces aliasing or at least controls the type of aliasing that is generated may be obtained in an elegant manner without having to rely on standard oversampling techniques.

The method provides a robust way to obtain efficient sampling and can reduce the risk of aliasing artifacts in the CT images.

According to a second aspect of the proposed technology, there is provided a system for data acquisition, for Computed Tomography, CT, based on an x-ray imaging system having a detector with a plurality of pixels, wherein the system is configured to perform data sampling with a temporal offset between measurements acquired by adjacent pixels of the detector.

According to a third aspect of the proposed technology, there is provided a Computed Tomography, CT, system comprising a system according to the second aspect.

According to a fourth aspect of the proposed technology, there is provided a computer program for enabling, when executed by a processor, data acquisition, for Computed Tomography, CT, using an x-ray imaging system having a detector with a plurality of pixels, wherein the computer program comprises instructions, which when executed by the processor cause the processor to perform data sampling with a temporal offset between measurements acquired by adjacent pixels of the detector.

According to a fifth aspect of the proposed technology, there is provided a computer-program product comprising a computer-readable medium having stored thereon a computer program according to the fourth aspect.

Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1B:
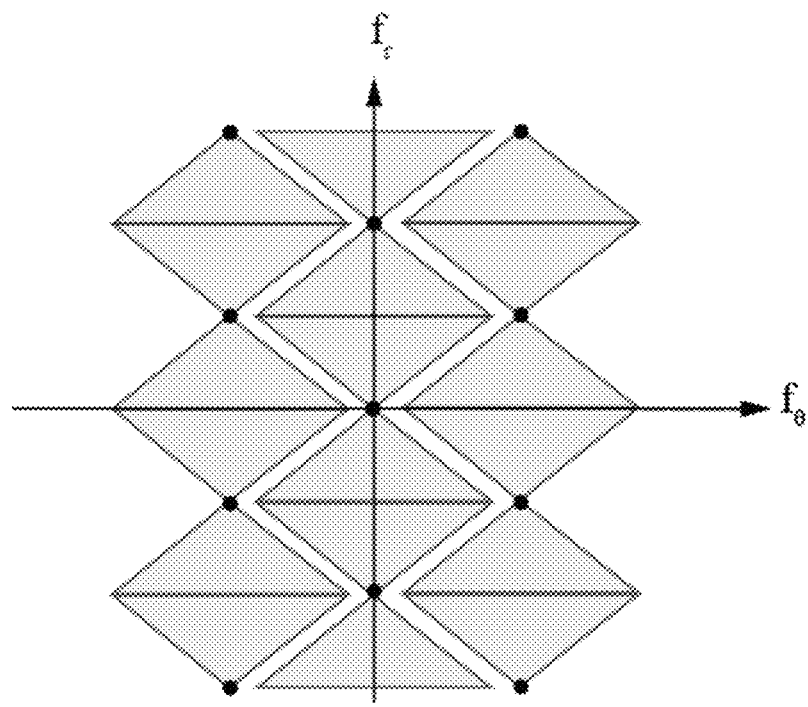
FIG. 1A and FIG. 1B are schematic diagrams illustrating the bowtie shaped spectral support of the sinogram and the nearest aliasing-free tiling of the Fourier spectra corresponding to rectangular sampling and hexagonal sampling, respectively.

As mentioned, the rapid development in the CT field makes increasingly high gantry rotation speeds and higher spatial resolution of the detectors possible; with this, the requirement for sufficient angular sampling increases. Insufficient angular sampling in CT leads to aliasing which destroys the reconstructed images by introducing streak-like artifacts from sharp edges.

The proposed technology suggests a unique and unprecedented data acquisition mechanism that manages aliasing in an effective manner.

According to a first aspect of the proposed technology, there is provided a method of data acquisition, for Computed Tomography, CT, based on an x-ray imaging system having a detector with a plurality of pixels, wherein data sampling is performed with a temporal offset between measurements acquired by adjacent pixels of the detector.

In this way, a custom sampling pattern, such as a hexagonal sampling pattern, e.g. one that reduces aliasing or at least controls the type of aliasing that is generated may be obtained in an elegant manner without having to rely on standard oversampling techniques.

The method provides a robust way to obtain efficient sampling and can reduce the risk of aliasing artifacts in the CT images.

By way of example, the data sampling of a new frame is initiated at different points in time for adjacent pixels.

For example, the data sampling comprises sinogram sampling in continuous rotation CT by temporally shifting frames acquired by adjacent pixels.

As an example, the data sampling may be performed to obtain a custom sampling pattern.

In a particular example, the data sampling may be performed to obtain a custom sampling pattern to reduce aliasing or at least to control the type of aliasing that is generated.

For example, the data sampling may be performed to obtain a hexagonal sampling pattern.

Alternatively, the data sampling is performed by applying a randomized temporal offset to the pixels.

In a particular example, the data sampling is performed with a temporal offset of half a frame time between measurements acquired by adjacent pixels.

For example, the data sampling may be performed by temporally offsetting every second pixel by half the frame time.

Optionally, the data sampling may be performed by temporally offsetting every ith pixel by a fraction of the frame time, where i is an integer equal to or greater than 2.

In a specific example, pixel i may be offset by (i−1)/N of the frame time, where i goes from 2 to N.

By temporally shifting the frames acquired by adjacent pixels on CT detector in continuous rotation, a custom sampling pattern of the 2D Radon transform is achieved. In an example embodiment of the invention, a hexagonal sampling pattern may be achieved by shifting the frames in every other pixel by half the frame time. Due to the nature of the CT data, hexagonal sampling can in theory relax the angular sampling criteria by a factor of two. The obtained effect is the same as that of two-times angular oversampling, without increasing the number of acquired measurements. The proposed method is feasible to implement and can have large impact for clinical high-resolution CT imaging. Evaluation is performed by simulation and by post-processing of clinical CT data.

Hexagonal sampling in 2D achieves optimal tiling of the Fourier spectra, thus reducing the risk for aliasing. This is particularly effective for a CT sinogram since the 'bowtie' shaped spectral support makes it suitable for tiling without spectral overlap. In theory, hexagonal sampling of the sinogram can reduce the angular sampling requirement by a factor of two.

According to an aspect of the proposed technology hexagonal sampling or similar custom sampling of the sinogram transform can be achieved in continuous rotation CT by introducing a temporal offset between the measurements acquired by adjacent pixels. The proposed method will be referred to as the temporally offset pixels (TOP) method.

Since the method does not require any major modifications to the imaging system, the approach can have high practical impact for high-resolution CT imaging and become as useful as flying focal-spot and quarter detector offset is today.

For a better understanding, the proposed technology will now be described with reference to particular, non-limiting examples.

As CT scanners operate at an increasingly high speed to fulfill the requirements of cardiac and perfusion imaging, and the spatial resolution of the detectors become higher, the angular sampling rate becomes more and more critical in order to avoid aliasing. Angular aliasing produces streaks from sharp edges that are devastating for the CT images. Increasing the angular sampling rate requires that the frame time of the detectors can be lowered and that the amount of produced data can be increased. Several oversampling techniques are today applied in clinical CT scanners in order to mitigate aliasing in both the radial and the angular direction.

The inventors have recognized that the manner in which the 2D Radon transform (the sinogram) is sampled plays a large role for avoiding aliasing.

When sampling in 2D, it is often beneficial to sample on a hexagonal grid since the sampling density is higher than when sampling on a Cartesian grid. In the Fourier domain, sampling on a hexagonal grid implies that the points from which the spectra is folded also lie on a hexagonal grid. Generally, this implies that the Fourier spectra can be stacked closer without the folded frequencies interfering with the original spectra. For CT, this is particularly true due to the nature of the spectral content of the sinogram; the essential spectra support for a sinogram has a 'bowtie' shape, which makes it especially suitable for stacking as seen in FIG. 1. Hexagonal sampling can in theory reduce the angular sampling requirement by a factor of two. The benefit of hexagonal sampling of the 2D Radon transform was described already in 1981 by Paul Rattey and Allen Lindgren (Sampling the 2-D Radon transform).

A hexagonal sampling grid in the sinogram can be achieved by applying one of several available oversampling techniques, e.g. flying focal-spot (FFS) in the x,y-plane and quarter detector offset with an odd number of frames over a full revolution (otherwise QDO has the same effect as adding another row of pixels shifted by half a pixel width). Oversampling techniques generally come with some complications such as having to track the focal spot movement or precisely controlling the relation between the number of frames and the rotation speed of the gantry (if you want the angular samples to match after 180 degrees).

Figure 1A:
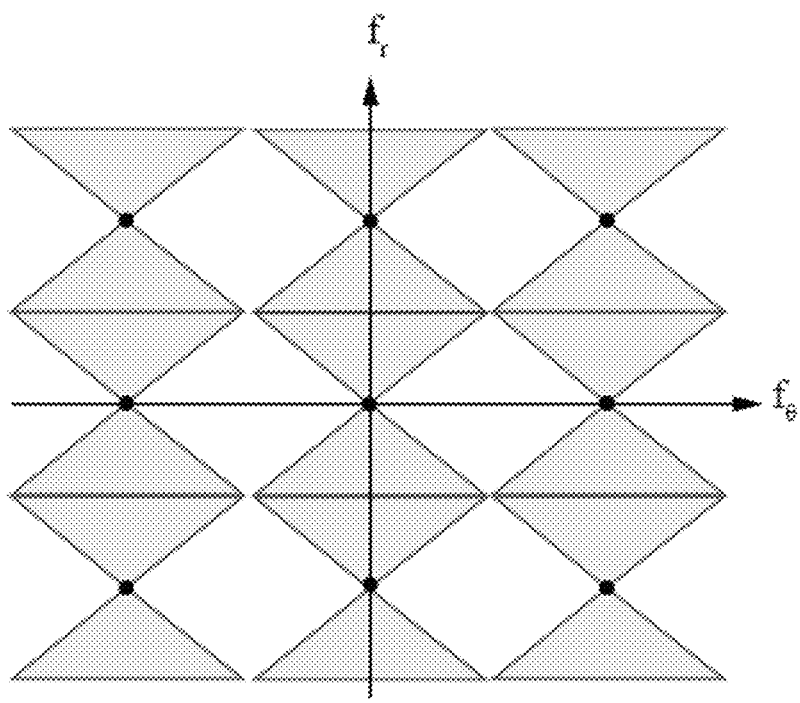

FIG. 1A and FIG. 1B are schematic diagrams illustrating the bowtie shaped spectral support of the sinogram and the nearest aliasing-free tiling of the Fourier spectra corresponding to rectangular sampling (FIG. 1A) and hexagonal sampling (FIG. 1B), respectively.

Here, among other things, we will show that hexagonal sampling can also be achieved in continuous rotation CT by introducing a temporal offset of half a frame time between measurements acquired by adjacent pixels in the transaxial plane. The inventors have never seen this approach being presented, nor explored in the prior art. The method is robust and can therefore have a large impact for high-resolution CT imaging.

Generally, the proposed technology provides a method and corresponding apparatus and computer program for acquiring a computed tomography image using an x-ray imaging system with a plurality of pixels, each acquiring a plurality of frames, where the acquisition of frames is made with at least one temporal offset between different subsets of pixels. In other words, different pixels initiates sampling of a new frame at different points in time.

By way of example, with a specific temporal offset, hexagonal sampling may be achieved. With other temporal offsets, other types of custom sampling may be achieved to reduce aliasing or at least to control the type of aliasing that is generated.

Normally, a pixel is an x-ray sensitive sub-element of the detector. Each pixel measures the incident x-ray flux as a sequence of frames. A frame is the total measured signal during a specified time interval.

The dimensions and segmentation of the detector array affect the imaging capabilities of the CT apparatus. A plurality of detector elements (also referred to as pixels) in the direction of the rotational axis of the gantry, i.e. the z-direction of FIG. 9 enables multi-slice image acquisition. A plurality of detector elements (also referred to as pixels) in the angular direction ($\xi$ in FIG. 9) enables measurement of multiple projections in the same plane simultaneously and this is applied in fan/cone-beam CT. Most conventional detectors are two-dimensional (sometimes called flat-panel detectors), meaning that they have have detector elements in the slice (z) and angular ($\xi$)directions.

Figure 10:
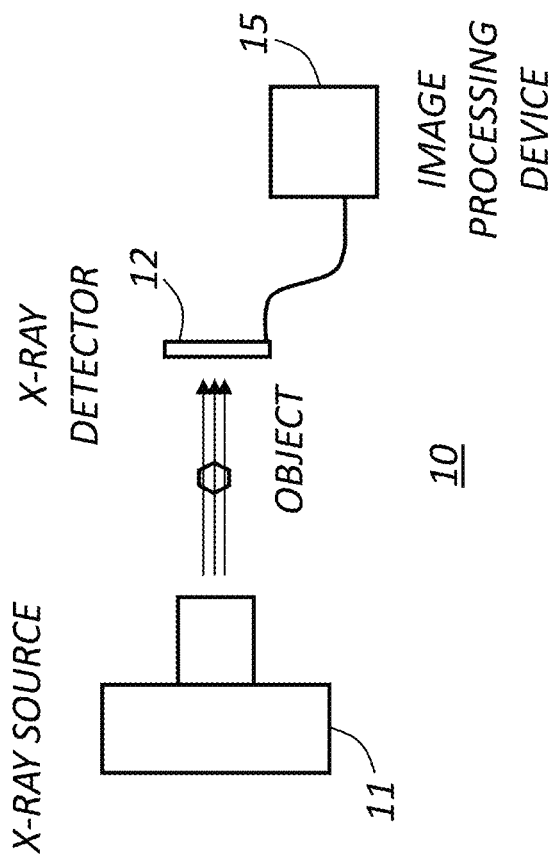
FIG. 10 is a schematic diagram illustrating an example of an overall x-ray imaging system.

For a given rotational position, each detector element (also referred to as a pixel) measures the transmitted x-rays for a certain projection line. Such a measurement is called a projection measurement. The collection of projection measurements for many projection lines is called a sinogram even if the detector is two-dimensional, making the sinogram a three-dimensional image. The sinogram data is utilized through image reconstruction to obtain an image of the interior of the imaged object. Each projection line (a point in the sinogram) is given by an angular coordinate, $\theta$, and a radial coordinate, r, as defined in FIG. 10. Each measurement with a detector element at a specific coordinate given by (r, $\theta$) is a sample of the sinogram. More samples in the sinogram generally lead to a better representation of the real sinogram and therefore also a more accurately reconstructed image.

Generally, the gantry rotates continuously and each detector element measures the x-rays flux within a frame time. A measurement period, T, is here defined as the interval in time during which a certain detector element is occupied with a measurement. The length of the measurement period can be, but does not have to be, equal to the frame time. The measurement period is much smaller than the total data acquisition time and multiple measurement periods follow directly after each other throughout the overall data acquisition/measurement. The length of the measurement period is referred to as the temporal sampling interval and the reciprocal of the sampling interval 1/T is referred to as the sampling frequency. The angular sampling interval of the CT system is given by the angular velocity of the gantry, $\omega = d\theta/dt$, and the temporal sampling interval, T, via $\Delta\theta = \omega T$.

Figure 11:
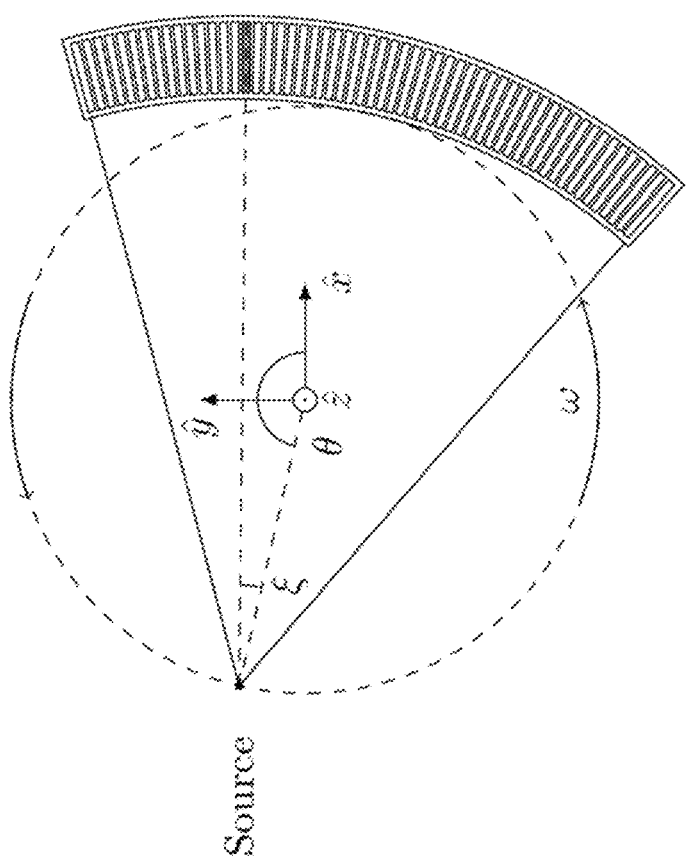
FIG. 11 is a schematic diagram illustrating an example of a CT geometry according to an embodiment.
Figure 12:
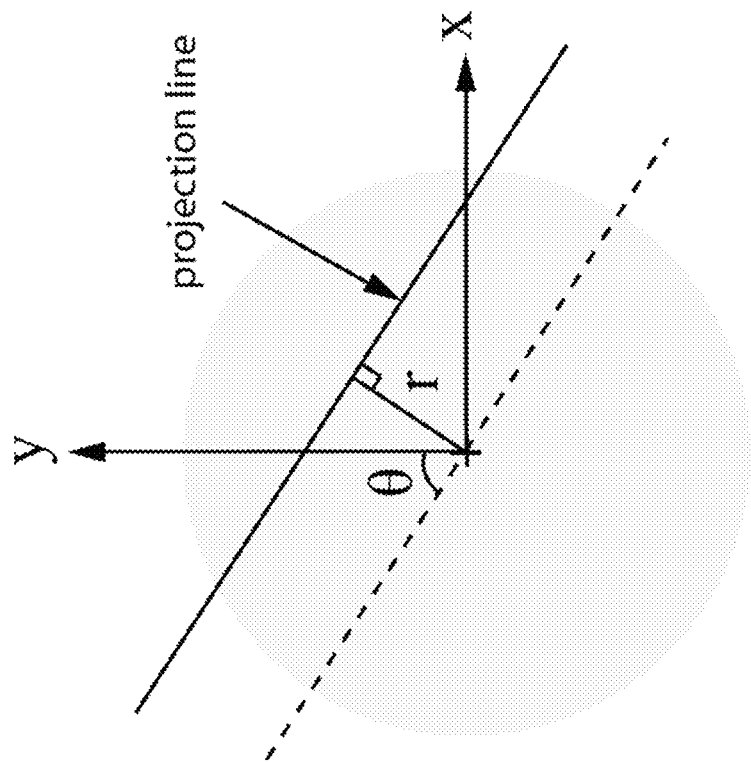
FIG. 12 is a schematic diagram illustrating an example of how each projection line is defined by an angular coordinate, $\theta$, and a radial coordinate, $r$.
Figure 13:
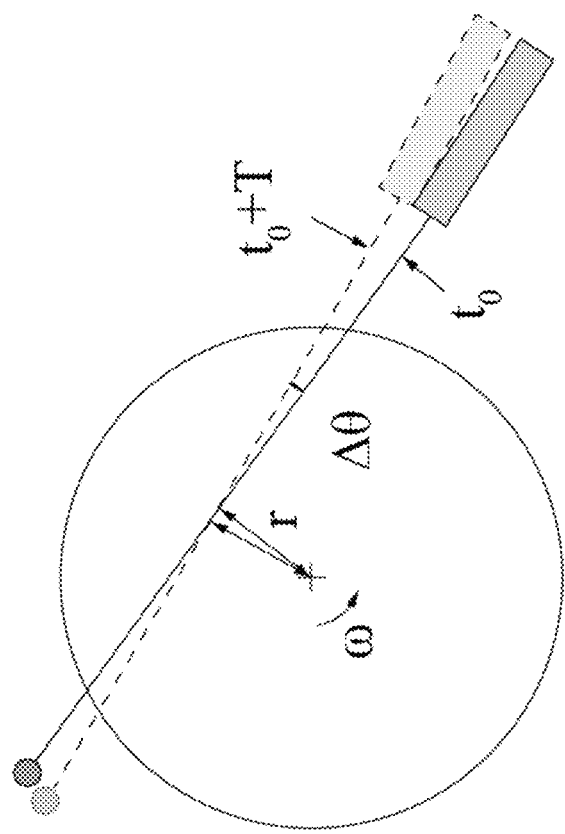
FIG. 13 is a schematic diagram illustrating an example of angular sampling, where the detector and the source are illustrated for two different positions separated in time by a sampling interval T.

A schematic example illustration of the angular sampling is displayed in FIG. 11, where the detector and the source are illustrated for two different positions separated in time by the sampling interval T. The radial coordinate for all projection lines corresponding to a specific detector element is invariant to the rotation of the gantry.

In order to perform an accurate image reconstruction from tomographic data, it is essential that there is a sufficient amount of angular samples. Insufficient angular sampling can lead to artifacts in the image, aliasing and poor resolution.

One way to increase the angular sampling frequency is to decrease the temporal sampling interval T. Decreasing the temporal sampling interval results in a corresponding increase in the amount of produced data.

Figure 4:
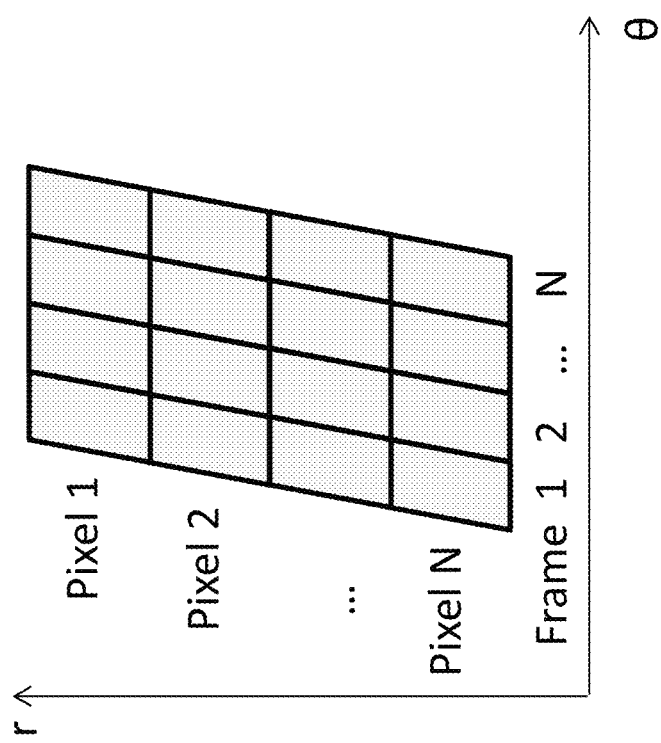
FIG. 4 is a schematic diagram illustrating an example of the relation between pixels and frames in sinogram space.

FIG. 4 is a schematic diagram illustrating an example of the relation between pixels and frames in sinogram space.

Figure 5:
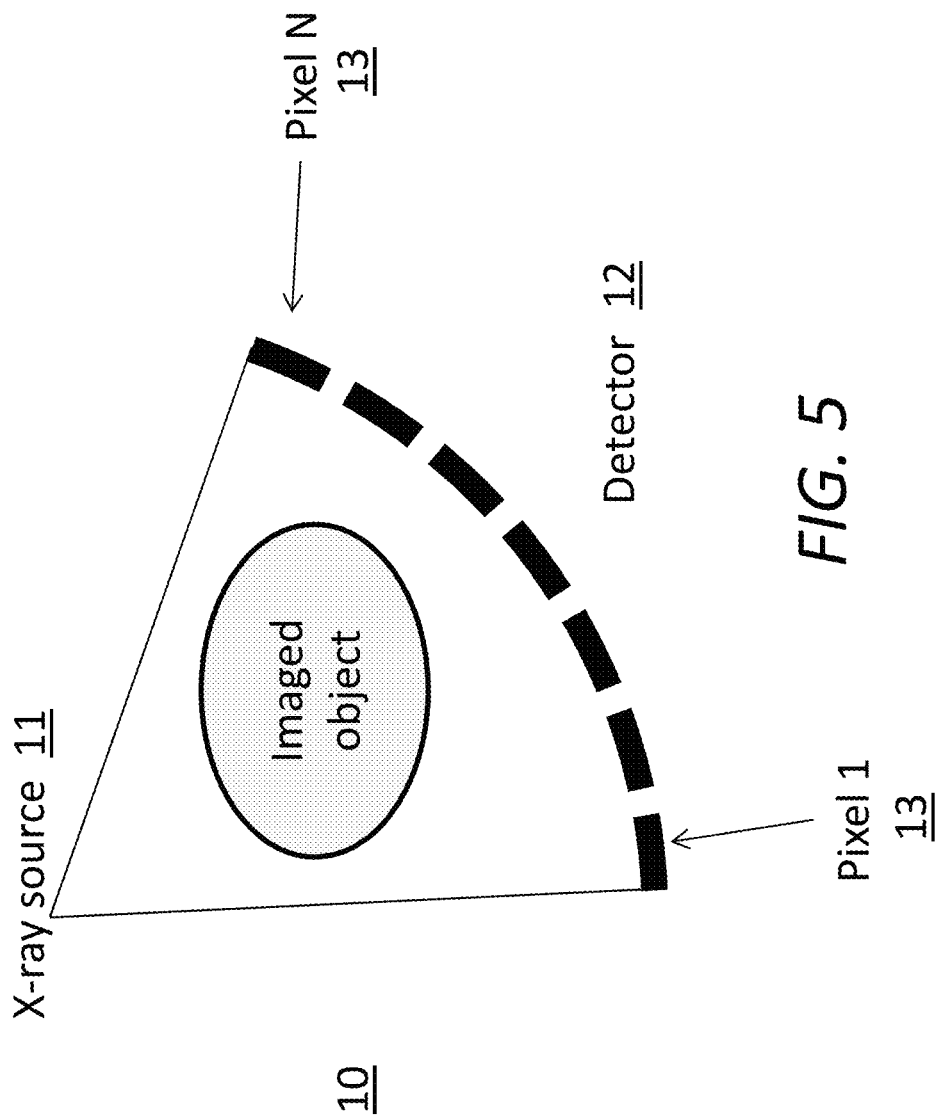
FIG. 5 is a schematic diagram illustrating an example of a CT system for 2D CT acquisition, where x-ray projection measurements may for example be made along projection rays lying in a single plane through the imaged object.

In a 2D CT acquisition, x-ray projection measurements may for example be made along projection rays lying in a single plane through the imaged object, as schematically illustrated in FIG. 5.

Figure 6:
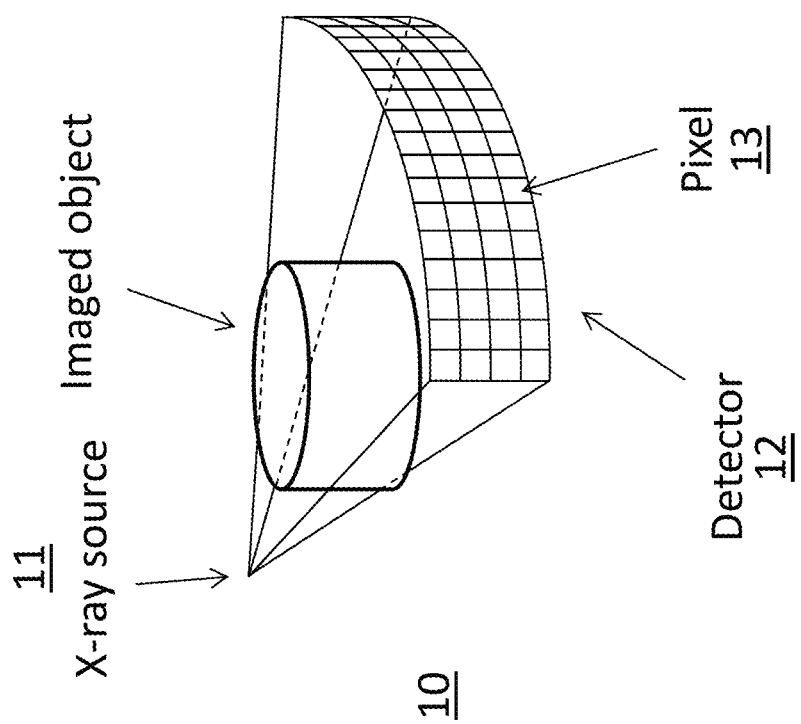
FIG. 6 is a schematic diagram illustrating an example of a CT system for 3D CT acquisition, where x-ray projection measurements may for example be made along projection rays passing through a three-dimensional sub-volume of the imaged object.

In a 3D CT acquisition, x-ray projection measurements may for example be made along projection rays passing through a three-dimensional sub-volume of the imaged object, as schematically illustrated in FIG. 6.

2D typically means that the measurements is performed in one and the same plane through the object to be imaged. In 3D, the measurements are performed in different positions along a direction orthogonal to the plane in which the source-detector pair rotates.

In fan beam CT, the pixels in the detector array sample the sinogram on a slanted line (dashed line FIG. 2) for each view (angular position). If the detector rotates with angular velocity ω and the frame time is Δt, the sampling positions are shifted a distance ωΔt in the angular direction between frames. By introducing a temporal offset of Δt/2 for every second pixel, hexagonal sampling of the sinogram is achieved.

Figure 2:
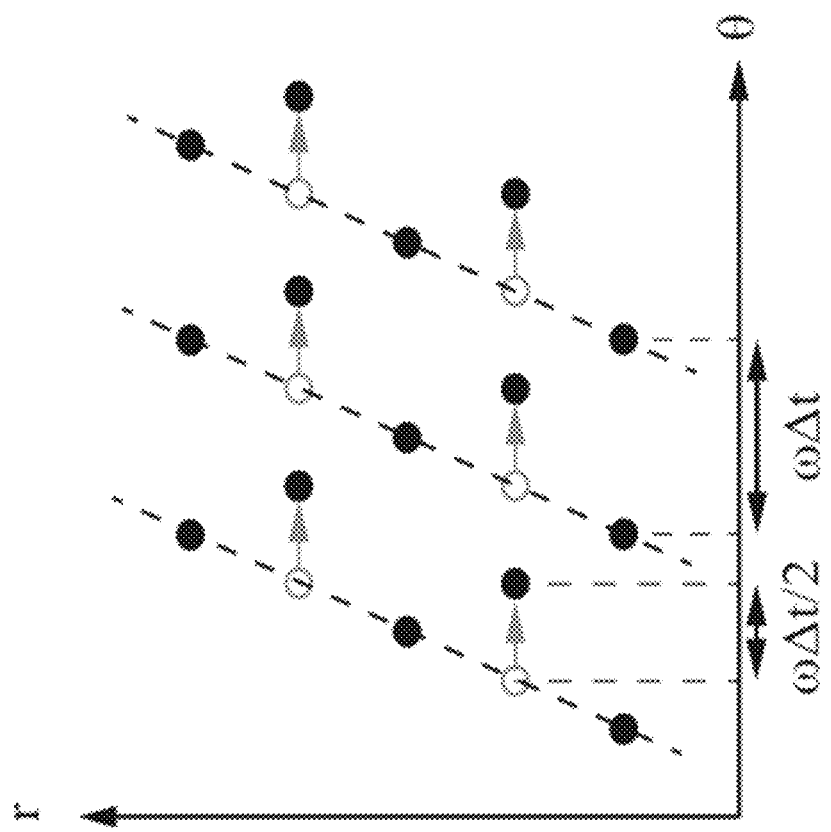
FIG. 2 is a schematic diagram illustrating an example of a hexagonal sampling grid achieved by temporally offsetting every second pixel by half the frame time.

FIG. 2 is a schematic diagram illustrating an example of a hexagonal sampling grid achieved by temporally offsetting every second pixel by half the frame time.

As a demonstration of the power of hexagonal sampling in the 2D radon transform, we have simulated a high-res sinogram from a single Gaussian point. The high-res sinogram was then down-sampled by a factor of two onto a 1) rectangular grid (removing every second sample in the angular direction) and 2) a hexagonal grid (removing ever second sample in the angular direction, but with the remaining angular samples shifted for adjacent radial positions). Both sinograms were then interpolated back onto the old high-res grid with a 2D linear interpolation. FIG. 2 shows the Fourier transform of the up-sampled sinogram corresponding to the a) rectangular sampling grid and b) hexagonal sampling grid. The angular aliasing produced by the rectangular sampling grid (the slanted lines in the corners) are not visible when the hexagonal sampling grid is used.

Figure 3B:
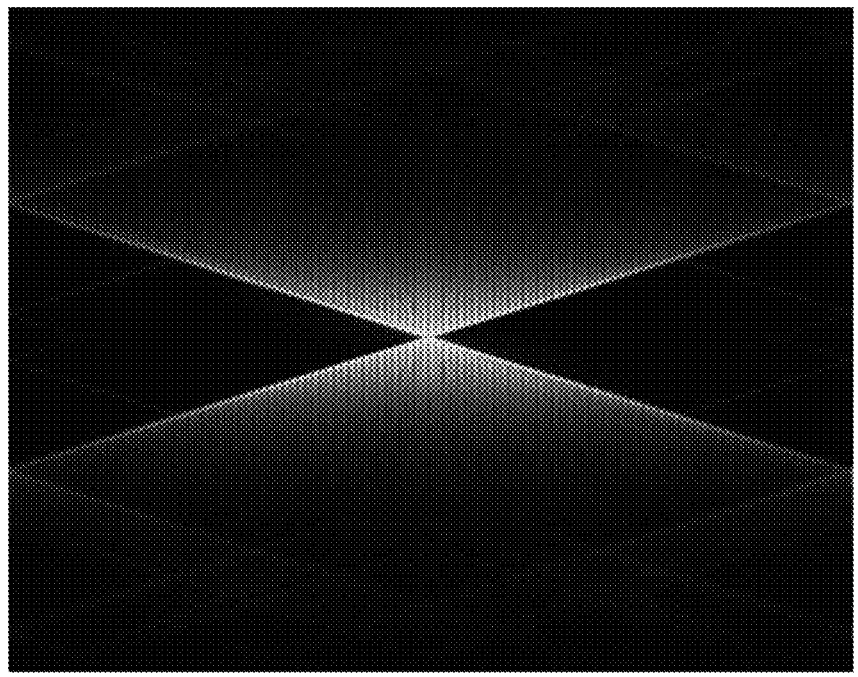
FIG. 3A and FIG. 3B are schematic diagrams illustrating an example of a 2D Fourier Transform of a sinogram from a Gaussian point sampled with rectangular sampling and hexagonal sampling, respectively.
Figure 3A:
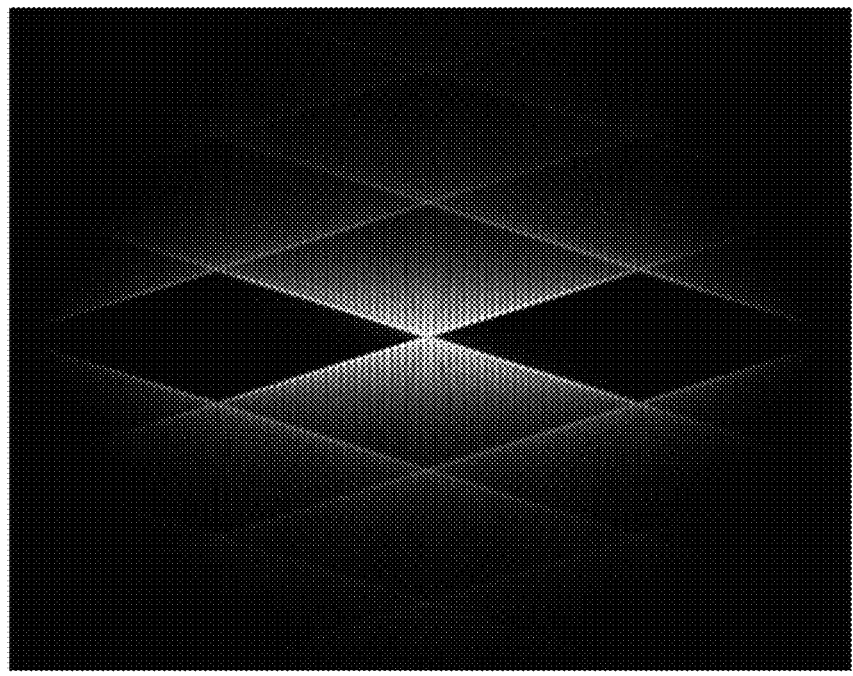

FIG. 3A and FIG. 3B are schematic diagrams illustrating an example of a 2D Fourier Transform of a sinogram from a Gaussian point sampled with rectangular sampling (FIG. 3A) and hexagonal sampling (FIG. 3B). The hexagonal sampling grid in FIG. 3B removes the extensive angular aliasing visible in FIG. 3A.

By way of example, the effect of the temporally offset pixels (TOP) approach may be demonstrated by post-processing of experimentally acquired CT data in order to evaluate the magnitude of the improvement in aliasing suppression in a situation similar to that of a clinical CT scanner.

Also, TOP can be combined with quarter detector offset (QDO) and/or flying focal spot (FFS) and the effect of a temporal offset in the z-direction on the detector may be demonstrated by simulations or practical experiments.

The method provides a robust way to obtain a more efficient sampling and can reduce the risk of aliasing artifacts in the CT images. In theory, the approach relaxes the angular sampling criteria (number of views needed to avoid aliasing) by a factor of two. The method will be evaluated on clinical CT data.

By temporally shifting the frames acquired by adjacent pixels on the CT detector, a hexagonal sampling of the 2D Radon transform is achieved. Due to the nature of the CT data, hexagonal sampling can in theory relax the angular sampling criteria by a factor of two. The obtained effect is the same as that of two times angular oversampling, however no extra measurements are necessary, which makes the proposed method more dose efficient. Also, the proposed technology may have large impact for high-resolution CT imaging.

Instead of temporally offsetting every second pixel by half the frame time, it is more generally possible to temporally offset every Nth pixel by a fraction of the frame time. For example, relative to pixel 1 which is not offset, pixel 2 is offset by 1/N of the frame time, pixel 3 is offset by 2/N of the frame time, and so on until pixel N, which is offset by (N−1)/N of the frame time. It may even be possible to apply a randomized temporal offset to the pixels.

Alternatively, it may also be possible to apply temporal offsets in the so-called z-direction, i.e. in the direction that is orthogonal to the plane in which the source-detector pair rotates.

It will be appreciated that the methods and devices described herein can be combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

In an aspect, there is provided an apparatus for sampling in Computed Tomography.

Figure 7:
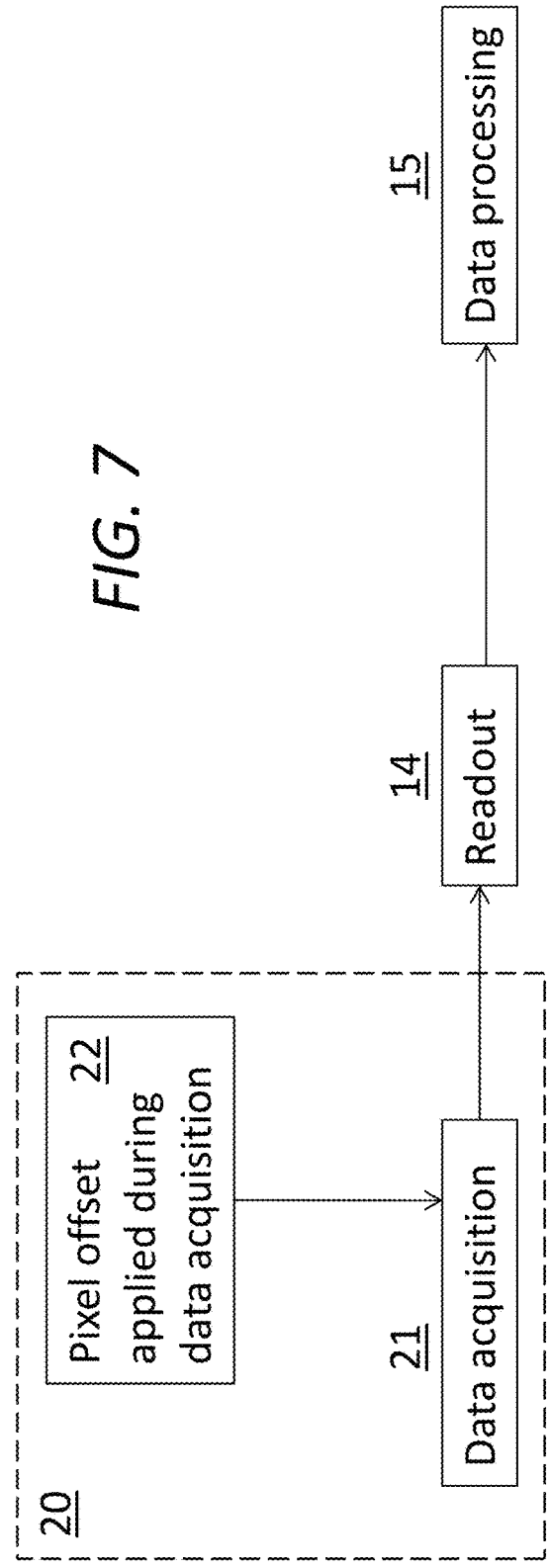
FIG. 7 is a schematic diagram illustrating a system for data acquisition and/or data read-out and/or data processing for Computed Tomography.

FIG. 7 is a schematic diagram illustrating a system for data acquisition and/or data read-out and/or data processing for Computed Tomography.

According to an aspect, there is provided a system 20 for data acquisition, for Computed Tomography, CT, based on an x-ray imaging system 10 having a detector 12 with a plurality of pixels 13. The system 20 is configured to perform data sampling with a temporal offset between measurements acquired by adjacent pixels of the detector.

According to another aspect, there is also provided a Computed Tomography, CT, system 10 comprising a system 20 for data acquisition as described herein.

By way of example, the system 20 may be configured to initiate sampling of a new frame at different points in time for adjacent pixels.

For example, the system 20 may be configured to perform sinogram sampling in continuous rotation CT by temporally shifting frames acquired by adjacent pixels.

As an example, the system 20 may be configured to perform the data sampling to obtain a custom sampling pattern.

In a particular example, the system 20 is configured to perform the data sampling to obtain a custom sampling pattern to reduce aliasing or at least to control the type of aliasing that is generated.

For example, the system 20 may be configured to perform the data sampling to obtain a hexagonal sampling pattern.

Alternatively, the system 20 may be configured to perform the data sampling by applying a randomized temporal offset to the pixels.

In a particular example, the system 20 is configured to perform the data sampling with a temporal offset of half a frame time between measurements acquired by adjacent pixels.

For example, the system 20 may be configured to perform the data sampling by temporally offsetting every second pixel by half the frame time.

Optionally, the system 20 is configured to perform the data sampling by temporally offsetting every ith pixel by a fraction of the frame time, where i is an integer equal to or greater than 2.

In a specific example, the system 20 may for example be configured to offset pixel i by (i−1)/N of the frame time, where i goes from 2 to N.

By way of example, each pixel 13 may be an x-ray sensitive sub-element of the detector 12, and the system 20 may be configured to such that each pixel 13 measures the incident x-ray flux as a sequence of frames, where a frame is the total measured signal during a specified time interval.

Figure 8:
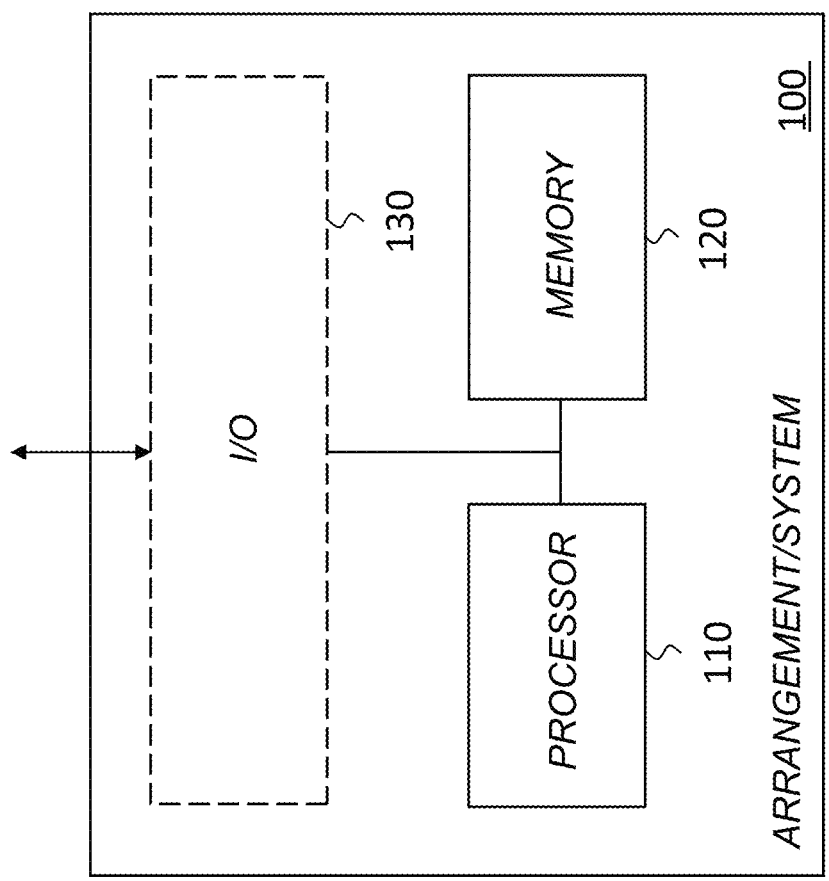
FIG. 8 is a schematic diagram illustrating an example of a processor-memory-based system for data acquisition according to an embodiment.

In a particular example, as illustrated in FIG. 8, the apparatus 100 comprises a processor 110 and a memory 120, the memory comprising instructions executable by the processor, whereby the processor is operative to perform and/or control the data acquisition. Optionally, the apparatus comprises an input/output interface for receiving input data and outputting resulting output data.

In this particular example, at least some of the steps, functions, procedures, modules and/or blocks described herein are implemented in a computer program, which is loaded into the memory for execution by processing circuitry including one or more processors. The processor(s) and memory are interconnected to each other to enable normal software execution. An optional input/output device may also be interconnected to the processor(s) and/or the memory to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

Figure 9:
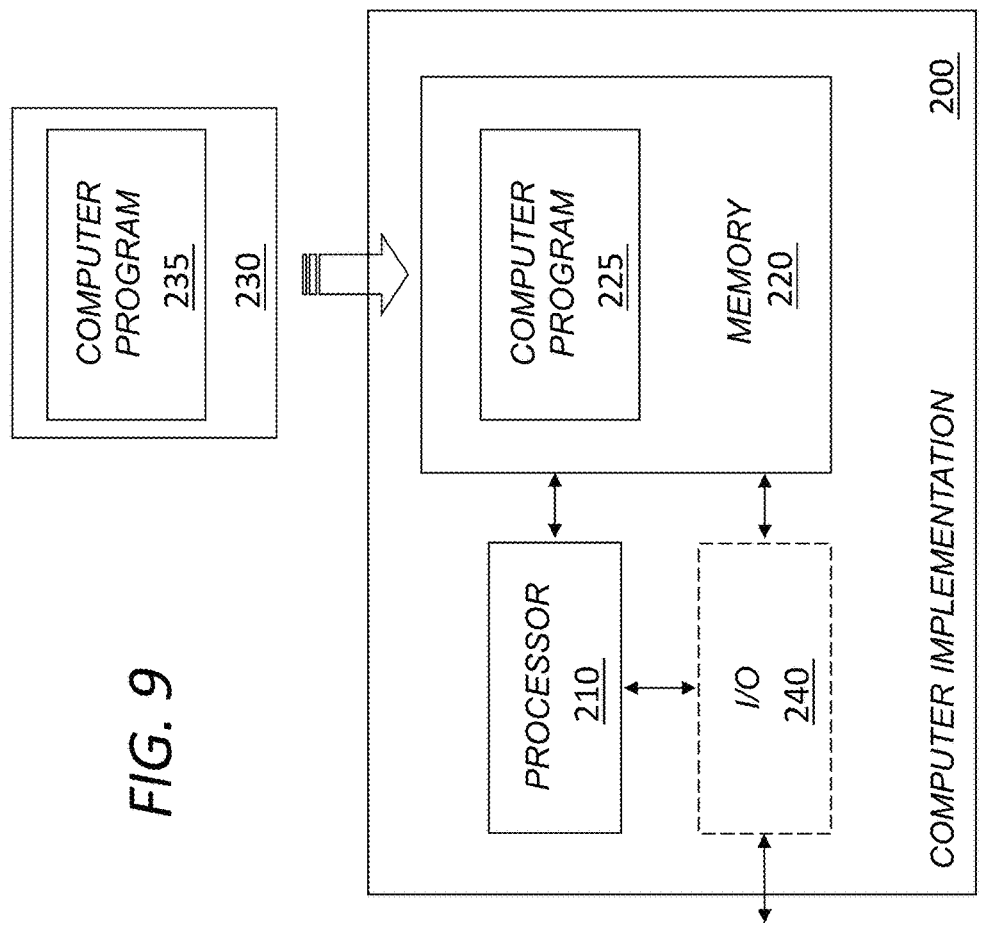
FIG. 9 is a schematic diagram illustrating another example of computer implementation according to an embodiment.

FIG. 9 is a schematic diagram illustrating another example of computer implementation according to an embodiment.

In another aspect, there is provided a computer program for improved sampling in Computed Tomography.

More particularly, there is provided a computer program 225; 235 for enabling, when executed by a processor 210, data acquisition, for Computed Tomography, CT, using an x-ray imaging system having a detector with a plurality of pixels, wherein the computer program 225; 235 comprises instructions, which when executed by the processor 210 cause the processor 210 to perform data sampling with a temporal offset between measurements acquired by adjacent pixels of the detector.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

The method flows presented herein may be regarded as a computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively it is possibly to realize the modules predominantly by hardware modules, or alternatively by hardware. The extent of software versus hardware is purely implementation selection.

It will be appreciated that the mechanisms and arrangements described herein can be implemented, combined and re-arranged in a variety of ways.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

The invention claimed is:

1. A method of data acquisition, for Computed Tomography, CT, based on an x-ray imaging system having a detector with a plurality of pixels, wherein the method comprises:
   a step of performing data sampling with a temporal offset between measurements acquired by adjacent pixels of the detector,
   wherein the data sampling is performed by applying a randomized temporal offset to the pixels.

2. A system for data acquisition, for Computed Tomography, CT, based on an x-ray imaging system having a detector with a plurality of pixels, wherein the system for data acquisition is configured to perform data sampling with a temporal offset between measurements acquired by adjacent pixels of the detector, wherein the system for data acquisition is configured to perform the data sampling by applying a randomized temporal offset to the pixels.

* * * * *